United States Patent [19] [11] 4,032,569
Onopchenko et al. [45] June 28, 1977

[54] PROCESS FOR CONVERTING CYCLOHEXANE TO ADIPIC ACID

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: July 14, 1975

[21] Appl. No.: 595,374

[52] U.S. Cl. ............................................. 260/533 C
[51] Int. Cl.² .................................... C07C 51/20
[58] Field of Search .............................. 260/533 C

[56] References Cited

UNITED STATES PATENTS 3,649,685 3/1972 Ishimoto et al. ............... 260/533 C Primary Examiner—Vivian Garner

[57] ABSTRACT

A process for converting cyclohexane to adipic acid which involves oxidizing cyclohexane with molecular oxygen in the presence of critical amounts of cobaltic ions in an aliphatic monobasic acid while maintaining critical temperature, pressure and contact time in the reaction zone.

10 Claims, No Drawings

PROCESS FOR CONVERTING CYCLOHEXANE TO ADIPIC ACID

BACKGROUND OF THE INVENTION

1. Field of the Invention

This invention relates to a process for converting cyclohexane to adipic acid which comprises oxidizing cyclohexane with molecular oxygen in the presence of critical amounts of cobaltic ions in an aliphatic monobasic acid solvent while maintaining critical temperature, pressure and contact time in the reaction zone.

2. Description of the Prior Art

In U.S. Pat. No. 3,231,608 Kollar describes and claims a process for converting cyclohexane to adipic acid in which cyclohexane is contacted with molecular oxygen in the presence of a cobalt salt of an organic acid in an aliphatic monobasic acid solvent. Unfortunately, the process of the patent results, generally, in relatively low conversions of cyclohexane to desired product.

SUMMARY OF THE INVENTION

We have found that significantly higher conversions of cyclohexane to a product predominating in adipic acid is obtained in the process defined above if critical amounts of cobalt are present in the reaction zone, the temperature and pressure during reaction are maintained within critical ranges and if the reaction is terminated within a critical time period.

The components required in the reaction zone are cyclohexane, an aliphatic monobasic acid solvent, cobaltic ions and molecular oxygen.

The solvent used herein can be any aliphatic monobasic acid containing only primary and secondary hydrogen atoms in its structure and having from two to eight carbon atoms, preferably having from two to four carbon atoms. Examples of satisfactory monobasic acid solvents for this reaction include acetic, propionic, normal butyric, caprylic, pelargonic, trimethylacetic, normal caproic acid, etc. Of these we prefer to use acetic acid. The molar ratios of solvent to cyclohexane lie between about 1.5:1 to about 10:1 or even higher, but preferably between about 3:1 to about 9:1.

Cobalt must be present in the form of its cobaltic ion. The source from which the cobaltic ion is obtained is immaterial, as long as cobaltic ions are maintained in the reaction mixture during the reaction period. Thus, as a source therefor any cobaltous or cobaltic salt of an organic acid can be employed, such as cobaltous or cobaltic acetate, propionate, naphthenate, etc. Of these we prefer to use the cobalt acetate salts. In order to assist in obtaining the high conversions herein, the amount of cobalt present in the reaction mixture is critical and must be in excess of about 25 millimols of cobalt per mol of cyclohexane, preferably in the range of about 50 to about 100 millimols of cobalt per mol of cyclohexane. Cobalt in an amount up to about 150 millimols per mol of cyclohexane can be used, but amounts in excess thereof produce no significantly improved results.

In the oxidation of cyclohexane with molecular oxygen there is a period of induction before the reaction begins to proceed. This period of induction is believed to occur in order to oxidize the cobaltous ion to the active cobaltic ion and to promote the production of free radicals from the cyclohexane charge. This induction period can vary, for example, from about ½ to as high as 3 hours, or even more. The induction period can be reduced, however, by the addition of an initiator to the reaction mixture. We believe the function of the initiator is to form free radicals faster than the cyclohexane will form free radicals and to act as an oxidant to convert the cobaltous ion into the active cobaltic ion. The initiator can be any compound in which oxygen has a valence of minus one or compounds which on reacting with molecular oxygen will form compounds which contain oxygen having a valence of minus one. Such compounds include, for example, ozone; inorganic peroxides, such as sodium or hydrogen peroxide; organic peroxides, such as benzoyl peroxides; peracids, such as peracetic acid; aldehydes, such as acetaldehyde; ketones, such as methyl ethyl ketone and cyclohexanone; and ethers, such as dimethyl ether. We prefer to employ cyclic hydroperoxides or cyclic ketones corresponding in carbon structure to the cyclic hydroperoxides and cyclic ketones produced in the reaction. The amount of initiator can vary between about 0.1 to about 20 weight percent based on the cyclohexane, with preferred amounts of initiator being between about 0.3 to about three weight percent based on the cyclohexane.

Free molecular oxygen must also be present in the reaction zone. Thus, either air or oxygen itself can be employed. Another critical requirement herein in obtaining high conversions of cyclohexane to adipic acid is the partial pressure of oxygen over the reaction mixture. We have found that such partial pressure must be at least about 150 pounds per square inch absolute (about 10.8 kilograms per square centimeter) and can be as high as about 1000 pounds per square inch absolute, or even higher (about 70.5 kilograms per square centimeter), but excellent conversions are obtained when the oxygen pressure is in the range of about 350 to about 600 pounds per square inch absolute (about 24.6 to about 42 kilograms per square centimeter). Such pressures, moreover, are sufficient to maintain the reactants in the liquid phase.

The reaction temperature is also critical and must be maintained in the range of about 85° to about 105° C., preferably in the range of about 90° to about 100° C. We have found that when temperatures in excess of the defined temperature ranges are employed there is an increasing tendency toward degradation of the desired adipic acid to glutaric and succinic acids. The reaction tends to go at an exceeding slow rate below the defined temperature ranges and would therefore be commercially unattractive.

We have also found that reaction time is also critical, in that a short reaction time, from about 0.5 to about three hours, preferably about one to about two hours is sufficient to obtain the desired high conversion. When the reaction mixture is permitted to remain at reaction conditions for periods in excess of those defined, the amount of additional conversion obtained is small and there is a tendency for the desired adipic acid to degrade to glutaric and succinic acids. Accordingly, when the desired reaction time is reached, reaction is terminated and recovery of product is effected. These reaction times are in addition to induction periods.

The reaction mixture is preferably well agitated to insure better contacting of the reactants. Agitation can be provided by mechanical stirring devices aided by the ebullition caused by the introduction of the oxygen-containing gas below the surface of the liquid reaction mixture.

At the end of the reaction period the reaction mixture can be separated into its component parts by any convenient means. Thus, the contents of the reaction zone are cooled to room temperature, depressured and the reaction mixture withdrawn from the reaction zone. The reaction mixture is diluted with an equal volume of water and then heated on a steam bath to a temperature of about 100° C. for about ½ hour, or until the solution is pink, indicating the presence of cobaltous ions, and then evaporated to dryness. The residue is extracted with acetone to separate the organic products from the catalyst. The organic products will contain the desired adipic acid and smaller amounts of glutaric and succinic acids. The individual acids can be separated from each other in any conventional manner, for example, by crystallization from conventional solvents such as benzene or water. The catalyst will, at least in part, be present as the cobalt salt of adipic, glutaric and succinic acids. To recover these acids from the catalyst, the catalyst is treated with sodium hydroxide to release the chemically-bound acids from the catalyst, at the same time converting the cobalt salt to its hydroxide or oxide state. Filtration will result in a solution containing the acids as their sodium salts. The latter are sprung with hydrochloric acid to form the desired free acids. Recovery of these acids is effected by evaporating the solution to dryness and then extracting the residue with acetone to separate the acids from sodium chloride. Evaporation of acetone will leave behind the additional adipic, glutaric and succinic acids. The catalyst can also be treated with concentrated hydrochloric acid and on evaporation to dryness will result in the formation of free organic acids and inorganic salts. These can readily be separated by extraction with a solvent, such as acetone mentioned above. In a continuous oxidation procedure, the amount of product acids tied up with the cobalt will reach a steady-state concentration, and for practical reasons can be ignored in calculations.

DESCRIPTION OF PREFERRED EMBODIMENTS

Example I

A series of runs was carried out in which all of the components of a reaction mixture, except molecular oxygen, were added to a 1-liter, stirred, 316-stainless steel autoclave. The contents of the autoclave were heated to desired temperature and pressured with molecular oxygen to desired pressure. Time between the moment when the reaction mixture is brought to the defined temperature and pressure levels and when oxygen absorption begins (indicating the start of oxidation) is defined as the induction period. The time between the start of oxygen absorption and when the reaction mixture is withdrawn from the reaction conditions is defined as reaction time. The products obtained were then subjected to recovery procedures as defined above. The data obtained are set forth below in Table I. Conversion was calculated by dividing the weight of the cyclohexane reacted by the weight of the cyclohexane charged times one hundred. Efficiency was based on the percent of cyclohexane reacted that was converted to the indicated compound.

TABLE I

| Run No. | 1 | 2 | 3 | 4 |
|---|---|---|---|---|
| Charge | | | | |
| Cobaltous Acetate Tetrahydrate, Millimols Per Mol of Cyclohexane | 24 | 24 | 95 | 95 |

TABLE I-continued

| Run No. | 1 | 2 | 3 | 4 |
|---|---|---|---|---|
| Cyclohexane, Grams | 70 | 70 | 70 | 70 |
| Methyl Ethyl Ketone, Grams | 15 | 15 | 15 | 15 |
| Acetic Acid, Grams | 420 | 420 | 420 | 420 |
| Reaction Conditions | | | | |
| Temperature, ° C. | 93 | 93 | 93 | 93 |
| Pressure, Pounds Per Square Inch Absolute | 205 | 500 | 205 | 500 |
| (Kilograms Per Square Centimeter) | (14.4) | (35.2) | (14.4) | (35.2) |
| Induction Time, Minutes | 19 | 18 | 30 | 35 |
| Reaction time, Hours | 2 | 2 | 2 | 2 |
| Product Data | | | | |
| Solids Recovered, Grams | 47 | 67 | 83 | 96 |
| Conversion, Per Cent | 39 | 56 | 70 | 79 |
| Selectivity To: | | | | |
| Adipic Acid, Per Cent | 84.0 | 81.2 | 82.6 | 77.0 |
| Glutaric Acid, Per Cent | 7.0 | 9.7 | 7.7 | 11.7 |
| Succinic Acid, Per Cent | 5.5 | 6.9 | 8.5 | 9.9 |
| Miscellaneous, Per Cent | 3.5 | 2.2 | 1.0 | 1.4 |

Runs Nos. 1 and 2 in Table I show that operation within the defined pressure range but with cobalt being present in amounts below the critical amounts results in less than desirable conversion of cyclohexane. Although the conversion in Run No. 2 was not as high as desirable, it will be noted that by merely raising the pressure to 500 pounds per square inch absolute in Run No. 2 from 205 pounds per square inch absolute in Run No. 1 the conversion was raised from 39 percent to 56 percent. The use of large amounts of cobalt and a pressure within the defined range in Run No. 3 resulted in a conversion of 70 weight percent of the cyclohexane. Further increase in pressure in Run No. 4 resulted in a further increase to 79 weight percent of the cyclohexane.

Example II

An additional set of runs was carried out, as above. The results obtained are tabulated below in Table II.

TABLE II

| Run No. | 5 | 6 | 7 |
|---|---|---|---|
| Charge | | | |
| Cobaltous Acetate Tetrahydrate, Millimols Per Mol Of Cyclohexane | 95 | 95 | 95 |
| Cyclohexane, Grams | 70 | 70 | 70 |
| Methyl Ethyl Ketone, Grams | 15 | 15 | 15 |
| Acetic Acid, Grams | 420 | 420 | 420 |
| Reaction Conditions | | | |
| Temperature, ° C. | 93 | 93 | 93 |
| Pressure, Pounds Per Square Inch Absolute | 500 | 500 | 500 |
| (Kilograms Per Square Centimeter) | (35.2) | (35.2) | (35.2) |
| Induction Time, Minutes | 25 | 30 | 35 |
| Reaction Time, Hours | 2 | 1.25 | 0.6 |
| Product Data | | | |
| Solids Recovered, Grams | 95 | 87 | 59 |
| Conversion, Per Cent | 80 | 73 | 50 |
| Selectivity To: | | | |
| Adipic Acid, Per Cent | 78.9 | 80.3 | 81.3 |
| Glutaric Acid, Per Cent | 10.5 | 10.0 | 9.5 |
| Succinic Acid, Per Cent | 9.4 | 8.2 | 8.3 |
| Miscellaneous, Per Cent | 1.2 | 1.5 | 0.9 |

The data in Table II show that under the critical reaction conditions herein a substantial amount of the reaction has occurred within a short time after reaction has begun and that at the end of two hours substantially all of the cyclohexane has been converted to desirable product.

EXAMPLE III

That it is imperative that reaction must be terminated within a short period of time and that the temperature of reaction cannot be permitted to rise above the critical ranges defined above is apparent from the following. In order to optimize the production of adipic acid herein, it became of interest to know whether or not adipic acid is stable under the conditions defined herein. A reasonable approach would be simply to add adipic acid to the cyclohexane oxidation charge and then determine the fate of the adipic acid. This approach, however, would not differentiate between the adipic acid added initially and the adipic acid produced as a result of oxidation. moreover, it might still be possible for adipic acid to be stable under the reaction conditions and products, such as glutaric and succinic acid, to form from cyclohexane by a different route.

To solve this problem we chose to study the oxidation of normal butane in the same system in the presence of adipic acid. Accordingly, the runs reported above were repeated except that the charge contained normal butane in place of cyclohexane and also adipic acid was present. The reactions were permitted to run until oxygen absorption ceased. The results are summarized below in Table III.

TABLE III

| Run No. | 8 | 9 | 10 | 11 |
| --- | --- | --- | --- | --- |
| Charge | | | | |
| Cobaltous Acetate Tetrahydrate, Millimols Per Mol of Normal Butane | 93 | 93 | 93 | 93 |
| Methyl Ethyl Ketone, Grams | 10 | 20 | 20 | 20 |
| Acetic Acid, Grams | 400 | 400 | 400 | 400 |
| Normal Butane, Grams | 50 | 50 | 50 | 50 |
| Adipic Acid, Grams | 30 | 30 | 30 | 30 |
| Conditions | | | | |
| Temperature ° C. | 94 | 104 | 115 | 130 |
| Pressure, Pounds Per Square Inch Absolute | 300 | 300 | 300 | 300 |
| (Kilograms Per Square Centimeter) | (21.2) | (21.2) | (21.2) | (21.2) |
| Induction Time, Minutes | 37 | 23 | 10 | None |
| Reaction Time, Minutes | 115 | 180 | 113 | 94 |
| Product Data, Grams (Selectivity) | | | | |
| Adipic Acid | 22.2(83) | 15.2(63) | 11.6(55) | 11.0(55) |
| Glutaric Acid | 2.1(8) | 2.9(12) | 3.1(14) | 2.8(14) |
| Succinic Acid | 2.4(9) | 5.9(25) | 6.6(27) | 6.2(31) |
| Recovery Data | | | | |
| Adipic Acid Degraded, Weight Per Cent | 20 | 41 | 49 | 49 |
| Per Cent Adipic Acid Degraded Per Hour | 10 | 13.6 | 26 | 31.2 |

The above data clearly show that it is critical to maintain the reaction at a temperature as low as possible and to terminate the reaction as soon as possible, for the amount of adipic acid degraded to glutaric acid and to succinic acid rises greatly with increasing temperature and longer residence times.

Obviously, many modifications and variations of the invention, as hereinabove set forth, can be made without departing from the spirit and scope thereof, and therefore only such limitations should be imposed as are indicated in the appended claims.

We claim:

1. A process for converting cyclohexane to adipic acid in a system consisting essentially of cyclohexane, an aliphatic monobasic acid solvent, cobaltic ions and molecular oxygen, which comprises subjecting cyclohexane to oxidation with oxygen in the presence of cobaltic ions in an aliphatic monobasic acid having only primary and secondary hydrogen atoms and having two to eight carbon atoms, wherein at least about 25 millimols of cobalt are present per mol of cyclohexane, while maintaining a temperature of about 85° to about 105° C. and an oxygen partial pressure of at least about 150 pounds per square inch absolute for a period of about 0.5 to about 3 hours.

2. The process of claim 1 wherein about 25 to about 150 millimols of cobalt are present per mol of cyclohexane.

3. The process of claim 2 wherein about 50 to about 100 millimols of cobalt are present per mol of cyclohexane.

4. The process of claim 1 wherein the temperature is in the range of about 90° to about 100° C.

5. The process of claim 1 wherein the oxygen partial pressure is in the range of about 350 to about 600 pounds per square inch absolute.

6. The process of claim 1 wherein the time of reaction is in the range of about one to about two hours.

7. The process of claim 1 wherein the monobasic acid has from two to four carbon atoms.

8. The process of claim 1 wherein the monobasic acid is acetic acid.

9. The process of claim 1 wherein the molar ratio of monobasic acid to cyclohexane is about 1.5:1 to about 10:1.

10. The process of claim 9 wherein the molar ratio of monobasic acid to cyclohexane is about 3:1 to about 9:1.

* * * * *